(12) United States Patent
Sabba

(10) Patent No.: US 12,397,140 B2
(45) Date of Patent: Aug. 26, 2025

(54) DEVICE, SYSTEM AND METHOD FOR SUBLINGUAL DELIVERY

(71) Applicant: Tema LLC, Rockville, MD (US)

(72) Inventor: Eitan Philippe Sabba, Rockville, MD (US)

(73) Assignee: Tema LLC

( * ) Notice: Subject to any disclaimer, the term of this patent is extended or adjusted under 35 U.S.C. 154(b) by 698 days.

(21) Appl. No.: 17/475,337

(22) Filed: Sep. 14, 2021

(65) Prior Publication Data
US 2022/0080167 A1 Mar. 17, 2022

Related U.S. Application Data

(60) Provisional application No. 63/078,475, filed on Sep. 15, 2020.

(51) Int. Cl.
*A61M 31/00* (2006.01)

(52) U.S. Cl.
CPC ..... *A61M 31/00* (2013.01); *A61M 2202/0468* (2013.01); *A61M 2205/103* (2013.01); *A61M 2205/3303* (2013.01); *A61M 2205/3368* (2013.01); *A61M 2205/3379* (2013.01); *A61M 2205/3584* (2013.01); *A61M 2205/502* (2013.01); *A61M 2210/0643* (2013.01)

(58) Field of Classification Search
CPC .......... A61J 7/0053; A61M 2210/0643; A61M 5/31581; A61M 31/00
See application file for complete search history.

(56) References Cited

U.S. PATENT DOCUMENTS

| | | | |
|---|---|---|---|
| 6,302,160 B2 | 10/2001 | Castellano | |
| 6,599,272 B1 * | 7/2003 | Hjertman | A61M 5/31581 604/209 |
| 6,913,592 B2 | 7/2005 | Parsons | |
| 7,089,934 B2 | 8/2006 | Staniforth et al. | |
| 7,780,637 B2 | 8/2010 | Jerde et al. | |
| 8,617,109 B2 | 12/2013 | Kronestedt et al. | |
| 9,861,578 B1 | 1/2018 | Busiashvili | |
| 10,188,585 B1 | 1/2019 | Busiashvili | |
| 10,238,577 B2 | 3/2019 | Gjertsen et al. | |
| 2008/0294096 A1 * | 11/2008 | Uber, III | A61M 31/005 604/66 |

(Continued)

*Primary Examiner* — Emily L Schmidt
(74) *Attorney, Agent, or Firm* — SOROKER AGMON NORDMAN RIBA

(57) ABSTRACT

A sublingual delivery device, system and method of operating such are provided. The sublingual delivery device comprises a device body comprising a delivery button configured to operate the sublingual delivery device, an ampoule carrying liquid, a threaded rod configured to push the ampoule towards a proximal end of the device body, a joints mechanism configured to convert vertical motion of the delivery button to horizontal motion of the threaded rod, an adjustment knob configured to set the volume of liquid to be delivered by adjusting a rotation degree of the knob, the knob located at a distal end of the device body, and a mouthpiece configured to be placed into a mouth of a user, the mouthpiece located at the proximal end of the device body, and the mouthpiece comprising a hollow needle configured to penetrate the ampoule and deliver liquid from the ampoule into the mouth of the user.

21 Claims, 6 Drawing Sheets

(56) References Cited

U.S. PATENT DOCUMENTS

| | | | |
|---|---|---|---|
| 2009/0224004 A1* | 9/2009 | Muller | B05C 17/0133 |
| | | | 222/326 |
| 2013/0030390 A1* | 1/2013 | Bonnadier | C08L 65/00 |
| | | | 606/223 |
| 2017/0027673 A1 | 2/2017 | Valentine | |
| 2019/0314580 A1* | 10/2019 | Kelly | A61M 5/31535 |
| 2020/0237622 A1* | 7/2020 | Campos | A61J 7/0046 |
| 2020/0261654 A1* | 8/2020 | Kühni | A61M 5/31 |
| 2023/0355884 A1* | 11/2023 | Bechtold | A61M 5/3157 |

* cited by examiner

DEVICE, SYSTEM AND METHOD FOR SUBLINGUAL DELIVERY

TECHNICAL FIELD

The present disclosure generally relates to sublingual delivery, and more specifically to a device, system and method for sublingual delivery of pharmaceutical compositions.

BACKGROUND

Medications are used as treatment for many illnesses. The routes of medication administration, whether self-administered or delivered by a health care professional, may vary. Inappropriate administration may be dangerous, whereas, knowledge and understanding may improve safety and effectiveness of drug therapy. Most importantly, careful attention should be given to the dosage of any taken drug.

The route of administration depends on three main factors: (i) the part of the body being treated; (ii) the way the drug is metabolized: and (iii) the formula of the drug. For instance, some drugs are degraded by stomach acid if they are taken through the mouth. Thus, such drugs may have to be administered by injection instead.

In sublingual delivery, the drug, which may come in the form of tablets, films or liquid, is delivered along the floor of the mouth through the mucosal membrane linings. The sublingual route takes advantage of the permeability of the oral epithelium via passive diffusion into the lipoidal membrane. The absorption of a drug administered sublingually is 3-10 times greater than when administered through the oral route. In addition, because sublingual venous drainage is systemic rather than portal, hepatic first-pass elimination can be avoided (e.g., bypassing gastric acid and intestine). The rapid absorption and onset of action of the sublingual route compared to the oral route are particularly useful for treating breakthrough pain as well as other medical situations that require immediate onset of therapeutic effect, thus making the sublingual route a promising alternative with high efficacy. Moreover, systemic drug delivery through the sublingual route offers different populations of patients such as pediatric, geriatric, psychiatric or patients who suffer from dysphagia (difficulty to swallow) an accessible route for enhanced management and compliance with their treatment regimen.

As explained hereinabove, sublingual administration of medicinal liquids is considered to be a promising alternative to the oral route. It is highly useful for rapid effect and is considered to be more patient compliant. However, current delivery systems and methods are imprecise and/or inconsistent and are mostly dependent on the administrator's technique, who might suffer from lack of dexterity or other physiological and physical limitations. Accidental dosing errors or inconsistent dosage are safety concerns that limit patient compliance with treatments and may result with poor health outcomes and even worsening of symptoms.

An additional problem with current systems and methods lies with lack of efficient communication between patients and their physicians or other health practitioners. Typically, patients are given a treatment regimen to be followed for a certain period of time by their physician, which should be followed up with future appointments every predetermined time interval. Unreliable communication may compromise the ability of physicians to evaluate treatment effectiveness, which translates to poor patient's management and health outcomes. Moreover, for patients with chronic, progressive disease, ongoing adherence to prescribed treatment regimens is often challenging. Medication non-adherence may result with poor health outcomes or even substantial worsening of the patient's condition.

It should also be noted that evidence is limited regarding the short- and long-term health effects of various liquid supplements and medicinal remedies, e.g., CBD/THC. Though the potential therapeutic benefits and use of CBD/THC is growing, there have not been enough largescale clinical trials that show, for example, that the benefits of the marijuana plant (as opposed to its cannabinoid ingredients) outweighs risks of using it in patients it is meant to treat. Data collection is important per a vast list of liquid medicines or supplements.

Accordingly, user-friendly and accurate sub-lingual delivery systems for delivering liquid medicine are critically required as well as adjunctive solutions to enhance patient management and improve care. Specifically, there is a need for a hand-held device, designed to dispense precise dosing with the flexibility to make self-adjustments by the patient on the basis of treatment results, together with recordkeeping of timing, dosing and other data like self-reported symptoms, which will potentially enhance patient's compliance and health outcomes as well as improve care by healthcare providers.

SUMMARY

According to an aspect of some embodiments of the present disclosure, there is provided a system and method for easy and user-friendly sublingual administration, which may be operated by the patient, a care-giver, a physician or a healthcare provider. In some embodiments, the sublingual delivery system of the present disclosure may be used for repeated sublingual delivery (preferably self-delivery) of specific dosage of cannabis oil, though any other medication or therapeutic agent in liquid form may be delivered via the sublingual delivery system of the present disclosure.

Sublingual products have been developed for numerous indications ranging from migraines, for which rapid onset of action is important, to mental illness, for which patient compliance is important for treating chronic indications such as depression and schizophrenia.

Pharmaceutical preparations for sublingual administration are manufactured in various forms, e.g., (i) sublingual tablets, which are tablets that rapidly dissolve in the mouth of the patient with little or no residue, for example, Nitroglycerine tablets or anti-emetic ondansetron;
  (ii) sublingual strips, which are similar to tablets in that they easily melt in the mouth and dissolve rapidly, for example: Suboxone;
  (iii) multi-purpose tablets, which are soluble tablets for either oral, buccal or sublingual administration, also suitable for preparation of injections, for example, Hydrostat (hydromorphone) and a number of brands of morphine tablets and cubes;
  (iv) sublingual drops, which comprise a concentrated solution to be dropped under the tongue, for example, Nicocodeine cough preparations, THC, CBD, allergen immunotherapy, and vitamins;
  (v) sublingual spray, which is a spray to be applied under the tongue, for example, Fentanyl; and (vi) lozenge, which effects a metered and patient-controlled-rate combination of sublingual, buccal, and oral administration, for example, Actiq fentanyl lozenge-on-a-stick (e.g., a lollipop).

Recent studies suggest that CBD may provide a safe, powerful natural treatment for many health issues. Sublingual is a popular choice for patients who would rather not inhale cannabis. For those who rule out vaping and smoking, either for personal health reasons or because they don't enjoy that type of administration route, sublingual administration offers the ideal substitute. It is one of the only non-inhaled options that can offer quick and long lasting (approximately 2-3 hours) relief from symptoms. Moreover, while edible cannabis effects might last throughout an entire day, the sublingual's effects will subside relatively quickly, allowing the patient to function and decide whether another dose is needed later along the day.

The present disclosure describes a reusable device designed to repeatedly deliver adjustable, accurate dose of liquid medicine sublingually, with a support system for patient engagement, data collection, and analysis. The device may record doses and timing in order to generate a log of use, allowing patients to monitor their dosage and reliably report to their healthcare provider. Moreover, healthcare providers may be able to monitor patient's compliance via the communicated log. The delivery device may be uniquely designed for accurate dose self-sublingual delivery of liquid medicine, which may be loaded in an ampoule, with minimal waste. The sublingual delivery device of the present disclosure may be ergonomically designed to allow use by people suffering from, for example, low fine motor dexterity or be used by healthcare providers. The sublingual delivery system of the present disclosure may comprise a mechanical (manual), electromechanical, or digital dial for adjusting the required dosage. The sublingual system may further comprise a timer (e.g., to count up to 60 seconds or other time periods) to indicate patients of the time required for the medicine in the oral mucosa to facilitate absorption. In some embodiments, the sublingual device may further comprise a replaceable mouthpiece made from a biocompatible material, e.g., medical silicone comprising an inner hollow needle, which may comprise a thin hollow tube with one sharp tip. The hollow needle may be made of glass or any type of crystalline material. The hollow needle may be covered by the softer biocompatible mouthpiece to avoid gum damage and allow for proper flow of products with different viscosity and flow properties from the device into the sublingual area of a patient.

In some embodiments, both the volume of dose delivered, as well as the timer may appear on a display, for example, a screen integrated on the device, e.g., an LCD screen. Volume accuracy of dosage may by measured by Linear variable differential transformer (LVDT) or linear and radial encoders with an accuracy of approximately 0.05 mm (which equals to 0.005 milliliter) or by a fine encoder that may be attached directly on the motor, in case of an electromechanical design, or on the main threaded rod, in case of a manual device. Another alternative may be to enable predetermined adjustable quantities that will initiate volume calculations to be presented on the screen. These features may also be controlled using a dedicated application on a computerized device, e.g., a mobile phone, a computer, a tablet, etc.

In some embodiments, the ampoules holding the medicine or therapeutic agent may also be made of glass, or a type of crystalline material, to maintain the physiochemical properties of the medicament or therapeutic agent. Specifically, the hollow needle may penetrate the ampoule to deliver the medicine into the oral cavity. Reloading of the ampoule may be easy and straight forward.

In some embodiments, the sublingual delivery device may be safely stored in an enclosed chargeable case, which may acquire, and store data collected by the device, monitor the temperature within the case in order to ensure proper storage temperature of the medicine carried within the sublingual delivery device. The case may even issue an alarm in case the temperature within it exceeds the maximum allowed temperature per medicine carried within the delivery device (i.e., the case and/or the device may provide temperature management).

In some embodiments, the sublingual delivery device may comprise communication capabilities to report all collected data to an application software that may store the data. The sublingual delivery device's processor may have the capability to monitor consumption, timing, remaining volume in the ampoule and other characteristics of the medicament of therapeutic agent (e.g., its temperature, expiration date) and so on. The processor may also lock the device to avoid leakage of medication when not in use. In some embodiments, the processor may further control setting dosage of the medication. e.g., via the display of the sublingual device, or via the computerized device that is in communication with the sublingual device. Analyzing modules may provide information on trend and statistics of usage per user.

In some embodiments, patients may manually record the status of their symptoms, via the dedicated application, in addition to data recorded automatically by the processor. All of the collected data may be stored in a cloud-based database and may be shared with healthcare providers through the Electronic Health Record (EH R) or research institutes. The collected data may be used to create largescale experimental groups to investigate treatment effectivity, improve personalized regimen, prediction algorithms, etc.

One aspect of the present disclosure is a sublingual delivery device comprising a device body having a proximal end and a distal end, the device body comprising: a delivery button configured to operate the sublingual delivery device; an ampoule carrying liquid; a threaded rod configured to push the ampoule towards the proximal end of the device body; a joints mechanism configured to convert vertical motion of the delivery button to horizontal motion of the threaded rod; an adjustment knob configured to set the volume of liquid to be delivered by the sublingual delivery device by adjusting a rotation degree of the knob, the adjustment knob located at the distal end of the device body; and a mouthpiece configured to be placed into a mouth of a user, the mouthpiece located at the proximal end of the device body, and the mouthpiece comprising a hollow needle configured to penetrate the ampoule and deliver liquid from the ampoule into the mouth of the user.

Optionally, the joint mechanism comprises a right vertical arm connected to a corresponding right arm, and a left vertical arm connected to a corresponding left arm. In some embodiments, the right and left arms are in turn connected to a ring arm that is horizontally pushed towards the distal end of the device body once the right and left vertical arms are vertically pushed by the delivery button.

Optionally, the device body further comprises a spring located between the adjustment knob and the threaded rod.

Optionally, the device body further comprises a display.

Optionally, the display displays the set volume of liquid to be administered by the sublingual delivery device.

Optionally, the display further displays a timer counting down a recommended time for holding the liquid in a sublingual cavity of the user, the recommended time is determined based on the type of liquid.

Optionally, the display displays the name of the liquid carried within the ampoule, the volume of liquid to be administered, the liquid volume carried by the ampoule, the volume remained in the ampoule, power source status of the sublingual delivery device, a timer, and/or any combination thereof.

Optionally, the device body further comprises a linear encoder configured to measure the location of the threaded rod, thereby to measure the amount of liquid that is delivered and the remaining volume of liquid carried within the ampoule.

Optionally, the device body further comprises a radial encoder configured to measure the rotation of the adjustment knob, thereby to measure the amount of liquid that is set to be delivered.

Optionally, the sublingual device is configured to provide an accurate volume of 0.05 mL with a variance of no more than 0.01 ml.

Optionally, the sublingual delivery device further comprises a processor configured to collect data related to time and volume of delivered liquid.

Optionally, the sublingual delivery device is configured to send the collected data to a computerized device in communication with said sublingual delivery device.

Optionally, the sublingual delivery device is controlled by a computerized device.

Optionally, the hollow needle is made of glass.

Optionally, the hollow needle is made of a crystalline material.

Optionally, the liquid carried within the ampoule may comprises one or more pharmaceutical compositions.

Another aspect of the present disclosure is a system for monitoring sublingual delivery, said system comprising: a sublingual delivery device as detailed hereinabove, a computerized device in communication with said sublingual delivery device; and a cloud-based database in communication with the computerized device, wherein the sublingual delivery device is configured to collect data, send it to the computerized device, and the computerized device is configured to send the data to be stored in the cloud-based database.

Optionally, the data comprises volume intake of the liquid, time of intake, remaining volume in ampoule, temperature or ampoule, expiration date of ampoule, user symptoms, user's physical state and/or any combination thereof.

Optionally, a physician or health care receives the collected data via the cloud-based database to monitor patient condition.

Another aspect of the present disclosure is a method for sublingual delivery, the method comprising: providing a sublingual delivery device as detailed above; setting a volume of liquid to be delivered by rotating the adjustment knob; placing the sublingual delivery device inside a sublingual cavity of the user; pressing the delivery button, thereby ejecting liquid from the mouthpiece through the hollow needle into the sublingual cavity; and receiving time and volume of delivered liquid via a computerized device in communication with the sublingual delivery device.

BRIEF DESCRIPTION OF THE DRAWINGS

Some non-limiting exemplary embodiments or features of the disclosed subject matter are illustrated in the following drawings.

In the drawings.

Figure 1:
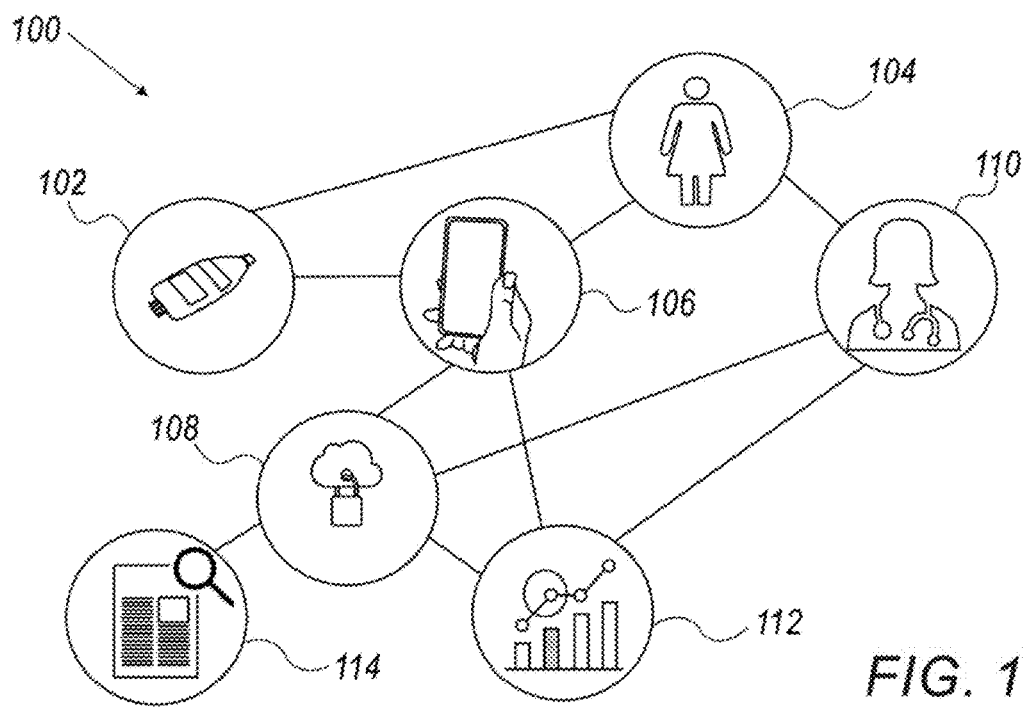
FIG. 1 is a schematic illustration of a sublingual delivery system, according to embodiments of the disclosure.

With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

Identical or duplicate or equivalent or similar structures, elements, or parts that appear in one or more drawings are generally labeled with the same reference numeral, optionally with an additional letter or letters to distinguish between similar entities or variants of entities, and may not be repeatedly labeled and/or described. References to previously presented elements are implied without necessarily further citing the drawing or description in which they appear.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

DETAILED DESCRIPTION

Some embodiments of the present disclosure provide a user with the ability to control the volume or dose of a medicament or therapeutic agent to be taken sublingually. Currently, available delivery methods, such as syringes, droppers, or sprays, fall short because they either deliver imprecise or inconsistent doses, are difficult to self-administer, and/or do not track nor monitor the patient's adherence and clinical outcomes.

The present disclosure provides a sublingual delivery device, system and method for enabling delivery to the sublingual glands, that is easy to use, and which is configured to provide an accurate dose or volume of liquid, each time it is operated by a patient or any other user. Data regarding dosage intake, time of intake, and patient's symptoms and physical state may be collected via the sublingual delivery device and/or its supporting system, i.e., a computerized device communicating with the sublingual delivery device. The collected data may then be transferred to a cloud-based database in order to be shared with physicians or healthcare providers of the user.

Before explaining at least one embodiment of the disclosure in detail, it is to be understood that the disclosure is not necessarily limited in its application to the details of construction and the arrangement of the components and/or methods set forth in the following description and/or illustrated in the drawings and/or the Examples. The disclosure is capable of other embodiments or of being practiced or carried out in various ways.

Reference is now made to FIG. 1, which is a schematic illustration of a sublingual delivery system, according to embodiments of the disclosure. System 100 for sublingual delivery may comprise sublingual delivery device 102, which may be configured to provide accurate volume of liquid to be applied under the tongue of a user. The liquid may comprise one or more pharmaceutical compositions. Device 102 may comprise a mouth applicator to be inserted into the mouth of a user, e.g., user 104. Device 102 may be connected to a software application via a computerized device 106, which may be used to control and set various parameters on device 102 and collect info regarding the operation of device 102. In some embodiments, the information collected by the application may be transferred via the computerized device 106 to a cloud-based database 108, from which the information may be sent to the user's physician 110 upon user authorization, or may be sent to be part of a research 114, for analyzing big data acquired from a large number of users of devices similar to device 102, e.g., evaluating treatment's long-term efficiency. In some embodiments, the collected data per user may be processed into processed data 112, which may be a log of usage of device 102 or may create individualized prediction models via machine learning and artificial intelligence algorithms, before it is sent to the physician 110 of the user 104 of device 102.

In some embodiments, device 102 may record the dosage (e.g., volume of liquid and timing) into the patient's log 112. The Log 112 may be available locally on the device 102 and may be downloaded into other storages like a computerized device 106, e.g., a personal computer or a mobile device, e.g., mobile phone, with or without designated software to read the data.

In some embodiments, log 112 upon user approval and registration, may be available on the patient's EHR (Electronic Health Record) to allow accessibility for the healthcare provider 110 in order to track the patient or user's progress. The data the healthcare provider 110 may be able to receive may comprise: a complete record of all taken dosages, alarms on anomalies in the general trend, correlation between the patient's data and a global data-base use case with the same case parameters.

Figure 2:
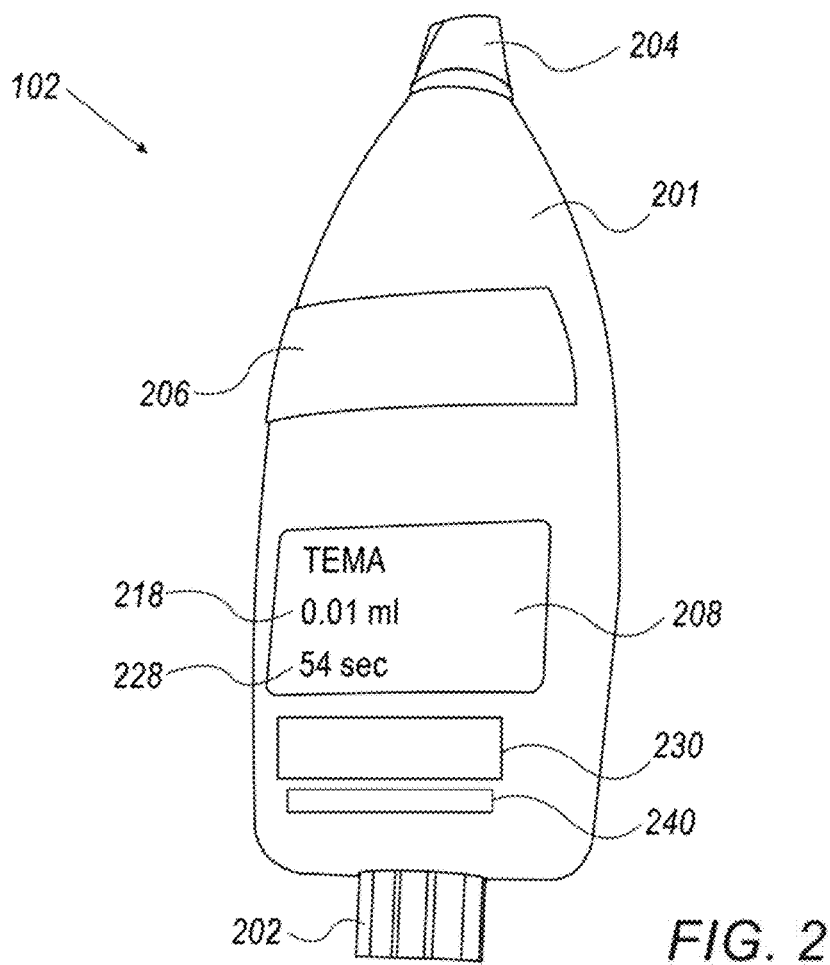
FIG. 2 is a schematic illustration of a sublingual delivery device, according to embodiments of the disclosure.

Reference is now made to FIG. 2, which is a schematic illustration of a sublingual delivery device, according to embodiments of the disclosure. In some embodiments, sublingual delivery device 102 may be ergonomically designed, while enabling self-handling and self-operation of users, even users who are challenged with fine motoric skills and/or suffer from functional disabilities, such as tremor. In some embodiments, the body 201 of device 102 may be made from stainless steel and/or aluminum, giving it durability and an esthetic appearance. In addition, stainless steel and aluminum have the advantage of being sustainable materials that are environmentally friendly. However, in other embodiments, body 201 may be made of other materials.

According to some embodiments, sublingual delivery device 102 may comprise a manual knob comprising dial 202 that may be manually turned by a user of sublingual delivery device 102 in order to adjust the proper volume or dosage to be taken by the user. In other embodiments, instead of a manual dial 202, sublingual delivery device 102 may comprise a digitally operated and controlled dial or other digitally operated dosage determining element. In other embodiments, sublingual delivery device 102 may comprise a linear or radial actuator.

The volume may be set up by the patient or user by turning the knob comprising a dial 202, which shows the dosage to be applied by the user. In case of an electromechanically controlled mechanism, the user can set the volume via the application operating on computerized device 106.

The sublingual delivery device 102 may provide accurate volume, for example, 0.05 mL=1/20 of Drop, with consistent repeatability and low variance, for example, variance of no more than 0.01 ml. Sublingual delivery device 102 may comprise a mouthpiece 204, which may be of a shape that conforms to the shape of a user and may be made from a relatively soft biocompatible material, since it is inserted into the mouth of a user, e.g., medical grade silicon. The material from which mouthpiece 204 may be made of, should be configured to prevent bacteria growth, e.g., medical grade silicon, and should be soft to protect the gum and sublingual surface of the patient.

In some embodiments, sublingual delivery device 102 may comprise a delivery button 206 that is to be operated by a user. e.g., by pushing, moving or pressing button 206. Once button 206 is operated, while mouthpiece 204 of sublingual delivery device 102 is placed into the mouth of a patient, the adjusted amount of liquid may be passed through the sublingual delivery device 102 and out through the mouthpiece 204 into the sublingual glands of a user. In some embodiments, device 102 may comprise a display 208, which may be an LCD screen or LED matrix. Display 208 may display the adjusted dosage 218 or volume quantity to be applied, as well as the remaining volume within device 102. Screen 208 may further display a timer 228 and any other required information. Immediately at the time of the delivery, the sublingual delivery device 102 may activate a timer 228, e.g., 0f 60 seconds, though other time periods may be implemented per type of liquid. The timer 228 may count the duration recommended to hold the medicine under the tongue for maximal absorbance and increased bioavailability.

In some embodiments, device 102 may comprise a power source 230. Power source 230 may be placed within device body 201 and may either be recharged by wires or wireless. In some embodiments, power source 230 may comprise batteries, which may or may not be rechargeable.

In some embodiments, sublingual delivery device 102 may comprise communication capabilities to report all collected data to an application software that may store the data. Sublingual delivery device 102 may comprise a processor 240, which may have the capability to monitor consumption, timing, remaining volume in the ampoule and other characteristics of the medicament of therapeutic agent (e.g., its temperature, expiration date) and so on. The processor 240 may lock the device to avoid leakage of medication when not in use. In some embodiments, the processor 240 may further control setting dosage of the medication, e.g., via the display of the sublingual device, or via the computerized device that is in communication with the sublingual device. Analyzing modules may provide information on trend and statistics of usage per user.

Figure 3:
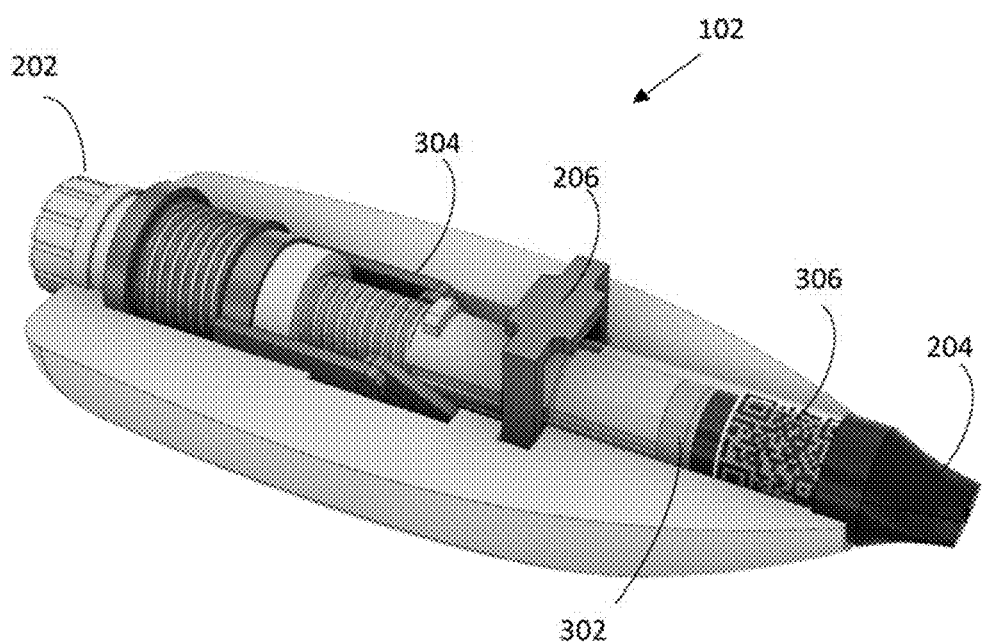
FIG. 3 is a schematic illustration of a sublingual delivery device without the upper cover, according to embodiments of the disclosure.

Reference is now made to FIG. 3, which is a schematic illustration of a sublingual delivery device without the upper cover, according to embodiments of the disclosure. Sublingual delivery device 102 may comprise, in addition to the manual dial 202, a plunger 302, which may be connected to a joints mechanism 304. Joints mechanism 304 may convert vertical movement of the user operating button 206 to horizontal movement of plunger 302. Sublingual delivery device 102 may further comprise an ampule 306 carrying the liquid medicament or therapeutic agent, from which liquid may be pushed out at the desired amount predetermined by the user via dial 202, through mouthpiece 204 and into the mouth cavity to be taken sublingually.

According to some embodiments, sublingual delivery device 102 may be carried and protected by a case or carrier (not shown). The case configured to carry sublingual delivery device 102 may comprise a first section into which device 102 may be placed and a second section into which ampule 306 may be inserted. The shapes of the first and second sections may be configured such that they hug the respective elements positioned within, i.e., device 102 and ampule 306. In some embodiments, the case or carrier of sublingual delivery device 102 may comprise charging capability, meaning that sublingual delivery device 102 may be charged while being positioned within its carrying case. In some embodiments, the carrying case may comprise temperature monitoring to monitor environment temperature such to ensure the ampule is held in proper low temperature that would not affect the chemical properties and efficacy of the liquid carried by ampule 306. In some embodiments, the carrying case may further comprise an alert system to provide notifications to the user, for example, in case there is an issue with respect to measured environment temperature, or to indicate that sublingual delivery device 102 is fully charged or when it is out of power. In some embodiments, the carrying case may be connected to a communication network and may allow transfer of information stored on the sublingual delivery device 102 to a computerized device, e.g., mobile phone 106 (FIG. 1), to the healthcare provider 110 (FIG. 1) or any other external receiver.

Figure 4:
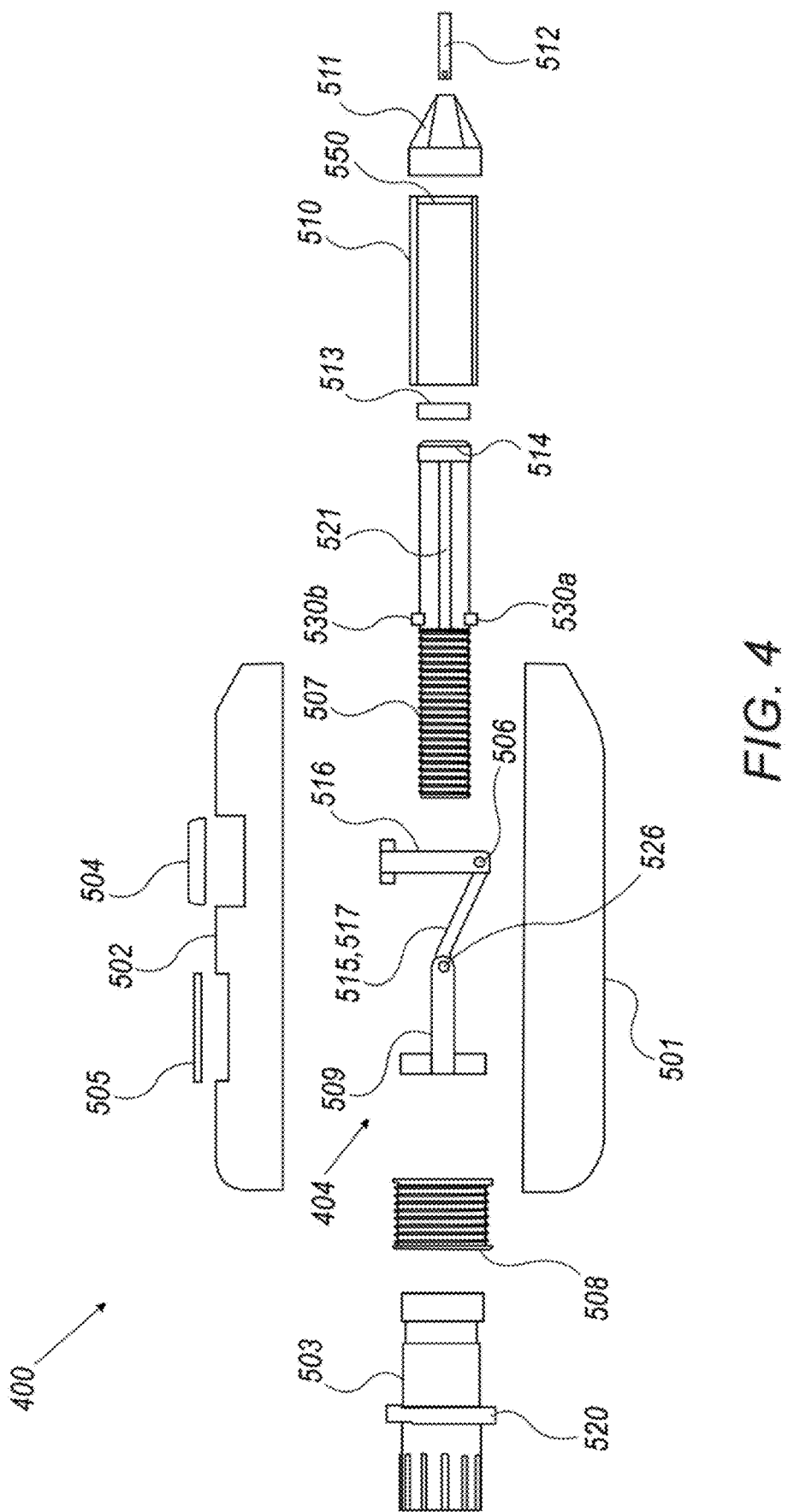
FIG. 4 is a schematic illustration of an exploded view of a sublingual delivery device, according to embodiments of the disclosure.
Figure 5:
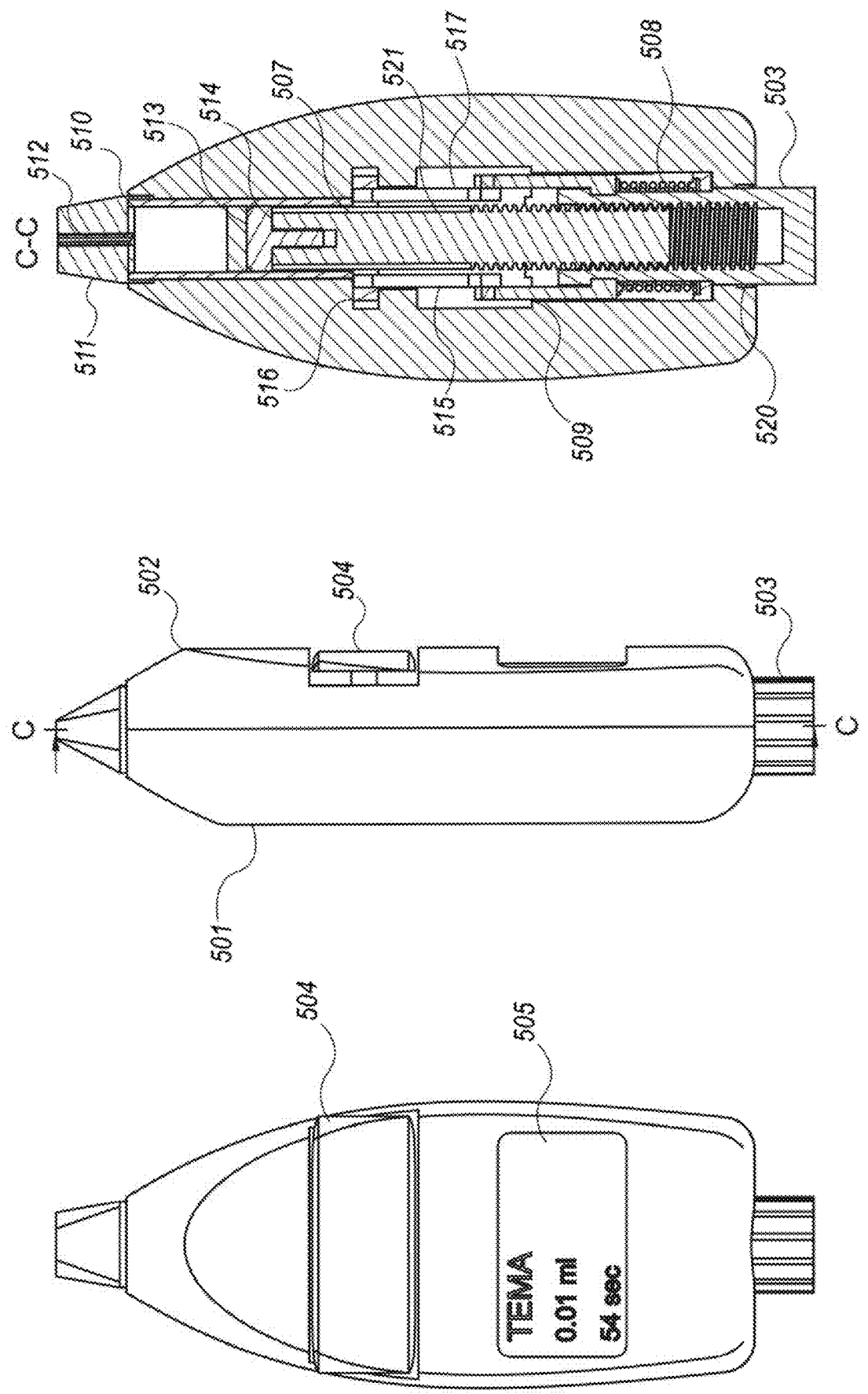
FIG. 5 is a schematic illustration of an upper view, side view and upper cross-section view of a sublingual delivery device, according to embodiments of the disclosure.
Figure 6:
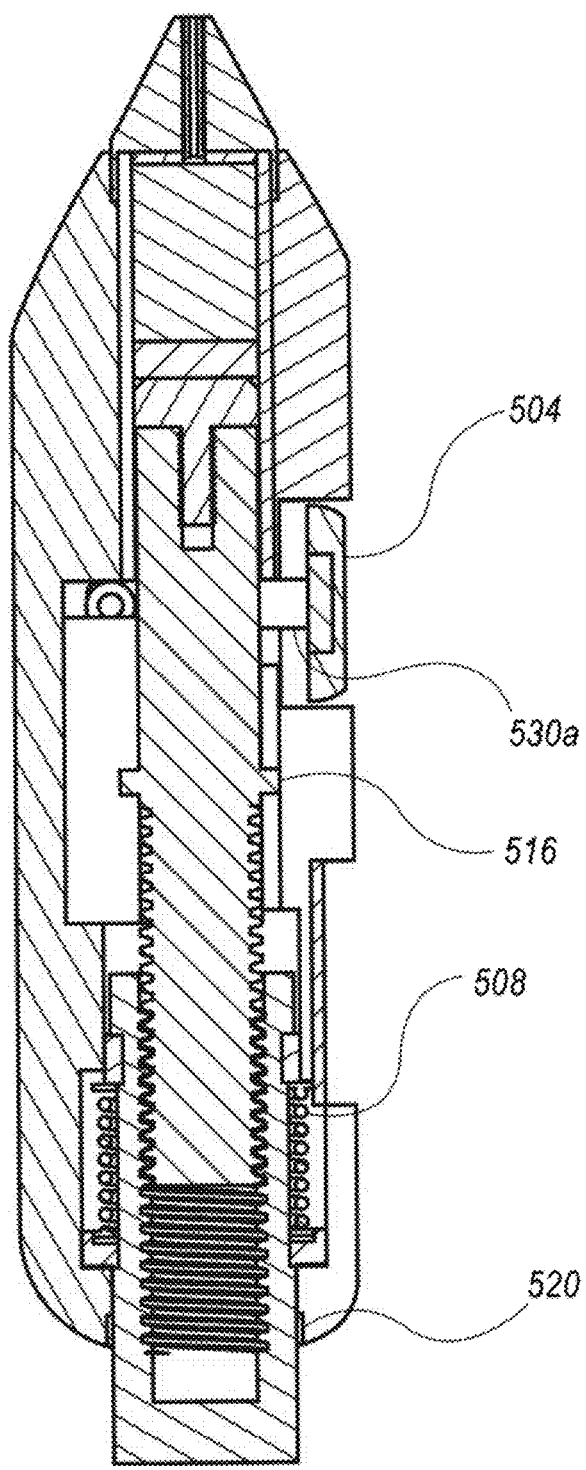
FIG. 6 a schematic illustration of a cross-section side-view of a sublingual delivery device, according to embodiments of the disclosure.

Reference is now made to FIGS. 4-6, which are schematic illustrations of an exploded view, an upper view, side view, upper cross-section view and a cross-section side-view of a sublingual delivery device, according to embodiments of the disclosure.

In some embodiments, sublingual delivery device 400 may be similar to sublingual delivery device 102 and may comprise similar components, such as a processor and a power source, in addition to the components detailed hereinbelow. In some embodiments, sublingual delivery device 400 may comprise a body base part 501, which may be connected to a body cover part 502 in order to create a closed body or housing, e.g., body 201 of device 102 (FIG. 2). Device 400 may comprise a dose adjustment knob 503 (similar to knob 202) and a delivery pressing button 504 (similar to button 206). Following adjustment of the required dose by adjustment knob 503, the delivery button 504 may be pressed to deliver the adjusted dose. Sublingual delivery device 400 may comprise a display 505 (similar to display 208), which may be, for example, an LCD screen. Display 505 may be powered by a power source, similar to power source 230 (FIG. 2). Display 505 may display various parameters on it, e.g., name of the liquid carried by the sublingual delivery device 400, volume of liquid to be delivered by device 400, volume remaining in device 400, a timer to indicate recommended time during which the liquid should maintain in the sublingual cavity, and power source status, i.e., how much power device 400 still has, or whether the power source is high or low.

Device 400 may comprise a piston and/or a threaded rod 507 which may be connected to an equilibrium spring 508 via a joints mechanism 404 (similar to joints mechanism 304, FIG. 3), which comprises elements 509, 515, 516 and 517. Joints mechanism 404 may convert vertical movement of delivery button 504, for example, when delivery button 504 is pressed vertically downwards, to horizontal movement of threaded rod or piston 507, which may comprise a plunger 514, towards the proximal end of device 400. Joints mechanism 404 may comprise ring arm 509 on one end and may further comprise left and right vertical arms 516 on an opposite end. Joints mechanism 404 may comprise a right side that is identical to its left side. Joints mechanisms 404 may comprise left arm 515, which may connect one side, e.g. the left side, of ring arm 509 to a left vertical arm 516. Left arm 515 may be connected to left vertical ring 516 via rotational joint 506 and may be connected to arm 509 via rotational joint 526. Joints mechanism 404 may further comprise a right arm 517 (located behind left arm 515) that may connect another side, e.g., the right side, of ring arm 509 to a right vertical arm 516 (that is located behind left vertical arm 516). Right arm 517 may be connected to left vertical ring 516 via rotational joint 506 and may be connected to arm 509 via rotational joint 526.

Once delivery button 504 is vertically pressed, left and right vertical arms 516 are pushed down, thereby pulling corresponding left arm 515 and right arm 517 down and towards the proximal end of device 400, which in turn pull ring arm 509 towards the proximal end of device 400. Ring arm 509 then pulls piston and/or threaded rod 507 as well as adjustment knob 503 along with it towards the proximal end of device 400.

In some embodiments, left and right vertical arms 516 may convert the pressing vertical movement of delivery button 504 to horizontal movement of piston and/or threaded rod 507 towards the proximal end of device 400, where an ampoule 510 which carries liquid is located. The liquid may comprise one or more pharmaceutical compositions. The liquid carried within ampoule 510 may be configured to be sublingually delivered to a user who is operating device 400, through a mouthpiece 511. Thus, operating delivery button 504 results in delivery of the liquid carried by ampule 510.

In some embodiments, device 400 may comprise a mouthpiece 511 (similar to mouthpiece 204, FIG. 2), which may be made of a biocompatible material, e.g., medical grade silicon. Mouthpiece 511 may comprise a hollow needle 512, e.g., a glass hollow needle, though other materials, e.g., crystalline materials, may be used to manufacture hollow needle 512. In some embodiments, when ampoule 510 is inserted into sublingual delivery device 400, hollow needle 512 may be configured to puncture a hole through the proximal end of ampoule 510. e.g., through a flexible ampoule cap 550, to allow exit of liquid therethrough.

In yet other embodiments, instead of mouthpiece 511 comprising hollow needle 512 configured to puncture an ampoule cap 550, ampoule 510 may comprise a one-way valve (not shown) located at its proximal end, such that when moveable ampoule seal 513 is pushed by plunger 514 into ampoule 510, the pressed liquid within ampoule 510 would cause the one-way valve to open and enable the predetermined dose of liquid to exit through it and thus to exit from device 400.

In some embodiments, after adjustment knob 503 is turned in the proper amount which is equivalent to delivering a predetermined dose of liquid, delivery button 504 may be vertically pushed or pressed and joint mechanism 404 may convert the vertical movement of delivery button 504 to horizontal movement of piston and/or threaded rod 507 towards the proximal end of device 400, as explained hereinabove. When piston and/or threaded rod 507 is pushed towards the proximal end of device 400, it may push plunger 514 towards ampule 510, thereby causing ampoule seal 513, which is located at the distal end of ampoule 510 and also adjacent to plunger 514, to be pushed into ampoule 510 in the exact amount dictated by adjustment knob 503. When ampoule seal 513 is pushed into ampoule 510, the predetermined dose of liquid is forced to exit through hollow needle 512 and into the sublingual cavity of a user.

In some embodiments, hollow needle 512 may be used to penetrate the ampoule cap 550 and may allow low friction and smooth flow of various liquids, even viscous liquids like CBD or THC oil. In some embodiments, the length of hollow needle 512 may be approximately 10-15 mm, i.e., approximately between 0.4-0.6 inches, with an inner diameter of between 0.5 mm-1 mm. In some embodiments, the volume that may be trapped in the hollow needle 512 may be between 0.008-0.012 ml, though other dimensions and thus other volumes may be implemented.

In some embodiments, the medicinal liquid, for example, CBD\THC oil may be stored in ampoule 510. In some embodiments, ampoule 510 may be made of glass, though other materials may be used.

In some embodiments, instead of via a needle, another way of connecting ampoule 510 to mouthpiece 511 is via a spring with a conical cup.

According to some embodiments, there may be several options for refilling the sublingual delivery device 400 (or sublingual delivery device 102). Among them, to replace a used and empty ampoule 510 with a new one, such that each ampule is for single use or is intended for several doses, e.g., between 20 to 50 doses, after which ampoule 510 is discarded; or to refill the ampoule, using, for example, a syringe that contains the same prescribed liquid, thereby causing the ampules to be reusable.

In some embodiments, instead of a manual mechanical mechanism of operation of sublingual delivery device 400, sublingual delivery device 400 may comprise an electromechanical mechanism to be initiated by pressing an operation button. A small motor or linear actuator may then press plunger 514, thereby applying the liquid carried by ampule 510. In such embodiments, there may be no need for applied force in pressing the operation button.

In some embodiments, the method of operating sublingual delivery device 400 may comprise several stages; (i) a loading stage, (ii) a dose setting stage, (iii) a delivering stage and (iv) a storage and data collection stage.

According to some embodiments, device 400 may be loaded with a liquid carrying element, e.g., ampoule 510. Device 400 may comprise several encoders, e.g., a linear encoder 521 that may measure the location of the threaded rod or piston 507 and thus measures the amount of liquid that is delivered and may further measure the current or remaining volume of liquid carried within the ampoule, and a radial encoder 520, which may measure the rotation of the adjustment knob 503 and thus measures the amount of liquid that is set to be delivered.

According to some embodiments, linear encoder 521 may measure the location of threaded rod or piston 507 relative to the location of body 501 and of knob 503. Accordingly, the location of threaded rod 507 with respect to ampoule 510 may be determined. i.e., how much threaded rod 507 is pressed into ampoule 510, which may indicate the amount of fluid there is in ampoule 510 since the initial amount carried by ampule 510 is known.

In some embodiments, encoders implemented as part of device 400, such as linear encoder 521 and radial encoder 520, may be used for calibrating device 400 as well as for routine checks.

In some embodiments, radial encoder 520 may measure the number of turns knob 503 is rotated by a user. Radial encoder 520 may measure the degrees at which knob 503 is turned and positioned at, at any time. The measured degrees may indicate the volume that may be delivered by calculating the length that threaded rod or piston 507 would undergo when turned by that measured degrees, depending on the pitch of the threads of threaded rod 507 and the diameter of the ampule 510. For example, if the thread pitch is 1 mm, a 360 degrees rotation may be equivalent to an increment of 1 mm. 1 milliliter equals 1 cubic centimeter, which equals 1000 cubic millimeter. If, for example, the diameter (D) of the ampule, e.g., ampule 510, is 12 mm, then the area of the ampule, which equals $2D/4 \times \pi$ is a total of 113 square millimeter. Thus, in this example, when rotating knob 503 at 360 degrees, threaded rod 507 may push or apply pressure against plunger 514 such to move 1 mm forward towards ampule 510. A 1 mm advancement against ampule 510 may be, for example, equivalent to the volume of 0.113 ml, by using the simple volume calculating equation of: Volume=H×Area, whereby H denotes the height, i.e., the distance ampule 510 is pushed at. Accordingly, the volume of liquid that is provided when ampule 510 is pushed by 1 mm (by turning knob 503 at 360 degrees) equals: volume=H×Area=1×113 square milimiter=0.113 milliliter. This is of course only one example, and different volumes may be provided when turning the knob 503 at 360 degrees or less, or for turning knob 503 more than one turn of 360 degrees, further depending on the diameter of the ampule, and the pitch of thread of the threaded rod 507.

In some embodiments, before placing an ampoule, e.g., ampoule 510 into device 400, there may be an ampoule scanning step, e.g., an RF ID ampoule scanning step, a QR code scanning step or scanning any other type of code, to identify contents of the ampoule and to validate that the selected ampoule is the one to be inserted into device 400, per a specific user. Scanning the ampoule tag may also provide information with respect to setting parameters of the sublingual delivery device 400 per the characteristics of the contents of the ampoule. For example, the type of medicinal liquid carried within the ampoule, the viscosity of the liquid, the temperature the ampoule should be stored at, the expiration date of the ampoule, and so on.

During the loading stage of device 400, the threaded rod 507 should be fully screwed into the dose adjustment knob 503, which may or may not comprise a dial. In case the threaded rod 507 is not fully inserted in the adjustment knob 503, the knob 503 should be turned clockwise until the threaded rod 507 is fully inserted into it and the knob 503 will reach maximum length, while pulling in the threaded rod 507. At this point, display 505 may display a word indicating it is the beginning of the operation process of device 400. For example, the word 'HOME' or 'STRAT' may appear on display 505.

During the volume or dose setting stage, the operating threaded rod 507 may be held by two keys or protrusions 530a and 530b located on both sides of threaded rod 507, which may slide along slots (not shown) that may be located on the inner sides of device body 501 and device cover 502. These keys 530a and 530b prevent threaded rod 507 from rotating. As knob 503 is turned, it may advance longitudinally in the direction away from ampule 510, i.e., screwing itself out of the body 501 of device 102, thereby pulling the joint mechanism 520, which may lift the button 504 upwards. The amount of liquid to be delivered may be measured by radial encoder 520, which may be an optical encoder. The amount to be delivered may be displayed on the screen 505.

At this initial state of determining dose, the user may load the ampule 510 into the device and attach the mouthpiece 511, which comprises a hollow needle 512, onto the device 400 next to the ampule 510.

The user may then turn the adjustment knob 503 counterclockwise and press the delivery button 504 until a small drop appears to come out of the mouthpiece 511. The device 400 is now loaded and ready to be used.

During the delivery stage, delivery button 504 is pressed, pushed or otherwise moved such to cause the joints mechanism 404 and adjustment knob 503 to be pulled forward towards the loaded ampule 510, thereby pressing and pushing the threaded rod 507 against the plunger 514 which pushes the ampule seal 513 into ampoule 510. Pushing ampoule seal 513 into ampoule 510 results in pushing the predetermined dose of liquid from the liquid carried by ampule 510 out of ampule 510 through the (glass) hollow needle 512. When a user operates button 504, e.g., by pressing it or pushing it, left and right vertical arms 516 are pushed down towards the device body 501. Left vertical arm 516 may be connected to left arm 515 and right vertical arm 516 may be connected to right arm 517 via a corresponding rotational joint 506. When vertical arms 516 are pushed down towards device body 501, vertical arms 516 pull left arm 515 and right arm 517 along with it towards the proximal end of device 400. Left arm 515 and right arm 517 may be further connected to ring arm 509 via a second rotational joint 526. Once left arm 515 and right arm 517 are pulled towards the proximal end of device 400, they pull ring arm 509 along with them. Ring arm 509 is pulled horizontally towards the proximal end of device 400, i.e., towards mouthpiece 511, piston and/or threaded rod 507 that is attached to ring arm 509 is caused to move with ring arm 509, thereby pushing threaded rod 507 against plunger 514, which leads to the release of the predetermined or selected dose of liquid out of ampule 510 through hollow needle 512 and into the sublingual cavity of the user, when mouthpiece 511 is located within such cavity.

The device 400 may notify the user when complete dose or liquid volume has been delivered and a timer (e.g., timer 228. FIG. 2) may be triggered for a predetermined time period depending on the type of liquid being administered. For example, the timer may count 60 seconds, though other time periods may be implemented.

In some embodiments, the user may choose the dose to be delivered by turning the knob 503 counterclockwise or clockwise.

In some embodiments, the user may place the mouthpiece 511 in the sublingual cavity and then operate device 400, e.g., by pressing the delivery button 504.

In some embodiments, a notification sound may be generated once the volume was delivered in full, which may initiate the timer. Once notified, the user may hold the device downwards and may view screen 505, displaying the countdown of the time period recommended for holding the liquid sublingually for proper absorption. For example, sixty seconds is often the recommended duration to hold the liquid in the sublingual cavity for it to be well absorbed.

During storage and data collection stage, in order to maintain the integrity of the ampule contents, the user may store the device in a carrying case, with a temperature sensor that may measure environmental temperature and may indicate when temperature is too high, too low, or adequate. The carrying case may also serve as a docking station with communication capabilities that receives and stores data collected by the device 400, and further transmits the data to a software application and stores it on a cloud database. In some embodiments, the carrying case may further be used to supply power to device 400 in case it includes electromechanical components.

In some embodiments, device 400 may display trends and other statistics, along with a log of doses and timing per user following processing of information, e.g., via analysis modules. Users or patients may also record descriptive information regarding their symptoms or general feeling via a computerized device, e.g., computerized device 106 (FIG. 1), such as a mobile phone or tablet. This may allow patients to monitor their usage of the liquid medicament or therapeutic agent that was prescribed to them (i.e., enhance adherence to treatment) as well as report reliable information to their healthcare provider (i.e., improve patient management and care).

Figure 7:
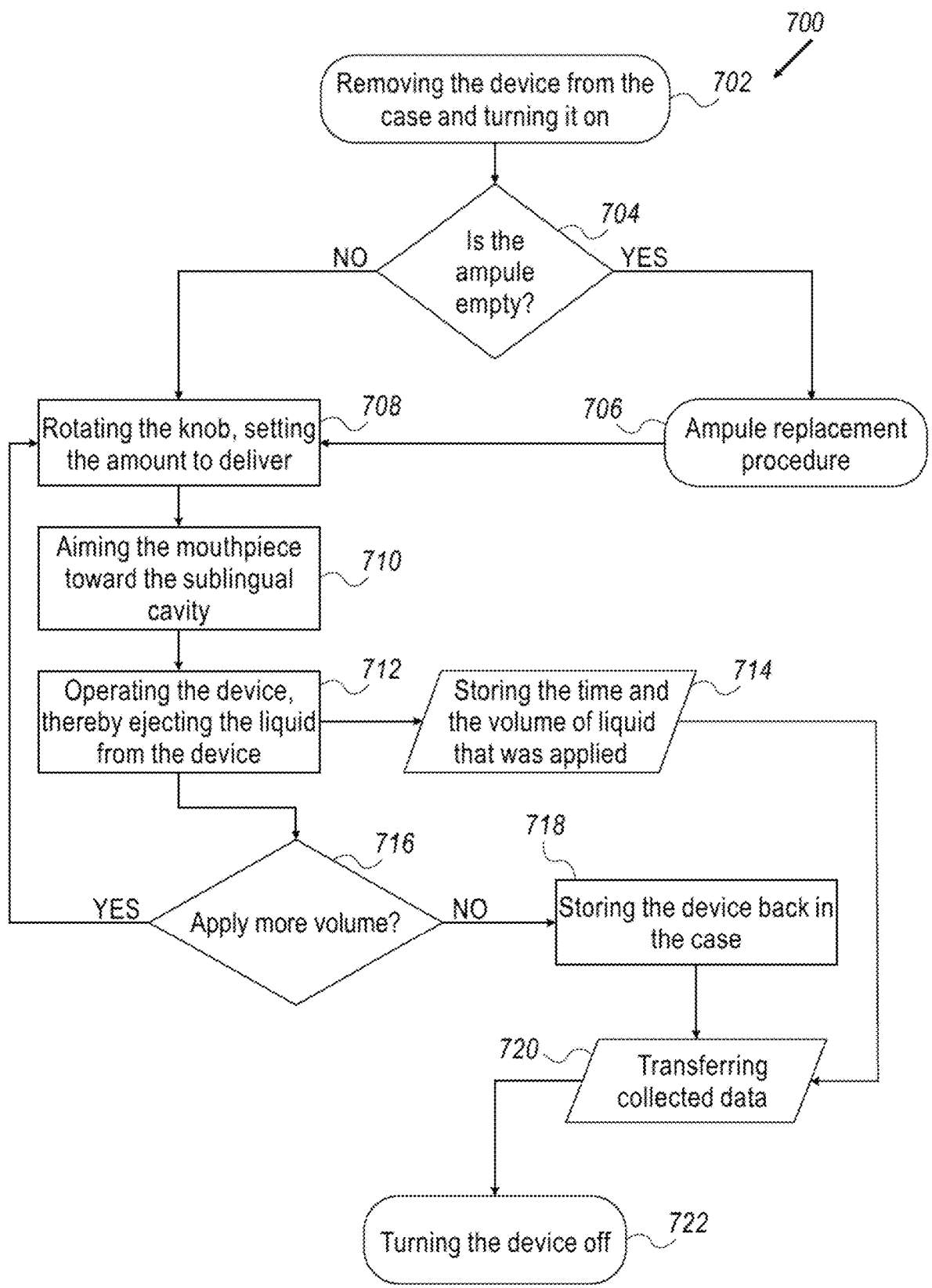
FIG. 7 is a schematic flowchart illustrating a method for sublingual delivery, according to some embodiments of the present disclosure.

Reference is now made to FIG. 7, which is a schematic flowchart illustrating a method for sublingual delivery via a sublingual delivery device, according to some embodiments of the present disclosure. In some embodiments, a method 700 for sublingual delivery may comprise operation 702, which may comprise removing a sublingual delivery device, e.g., device 102, or device 400 from its carrying case, and turning it on, e.g., by pressing a power button. It is then to be determined in operation 704 whether the ampule carried within the device, e.g., ampule 510, is empty. When the ampule is empty, a procedure for replacing the empty ampule with a new full ampule 706 takes place. When the ampule is not empty, method 700 may comprise operation 708, which may comprise rotating the knob, e.g., knob 503, counterclockwise, thereby setting the amount of medicament or therapeutic agent to be delivered. Method 700 may further comprise operation 710 comprising applying and aiming the mouthpiece, e.g., mouthpiece 511, toward the sublingual cavity of a user.

In some embodiments, method 700 may further comprise operation 712 comprising operating the sublingual delivery device, e.g., by pressing a button, e.g., button 504, down or inwards towards device body 501, thereby ejecting the liquid of the medicament or the therapeutic agent from the delivery device. According to some embodiments, method 700 may comprise operation 714, which may comprise storing the time of intake and the volume of liquid that was delivered by the device, e.g., device 102 or device 400.

In some embodiments, a user may require an additional dose as in operation 716. When a user requires an additional dose, method 700 continues by repeating operations 708 to 712 and operation 714. When the user does not require an additional dose, method 700 may comprise operation 718 comprising storing the device back in the carrying case.

In some embodiments, at the end of the delivery procedure, either after operation 714 or after operation 718, method 700 may comprise operation 720 comprising transferring the data collected during operation 714 to an external receiver, e.g., the user's mobile app or any other medium that may enable sharing the collected information regarding the delivery session with the user's caregiver. Method 700 may further comprise operation 722 comprising turning the delivery device off.

The flowchart and block diagrams illustrate architecture, functionality or an operation of possible implementations of systems, and methods according to various embodiments of the present disclosed subject matter. It should also be noted that, in some alternative implementations, illustrated or described operations may occur in a different order or in combination or as concurrent operations instead of sequential operations to achieve the same or equivalent effect.

The corresponding structures, materials, acts, and equivalents of all means or step plus function elements in the claims below are intended to include any structure, material, or act for performing the function in combination with other claimed elements as specifically claimed. As used herein, the singular forms "a", "an" and "the" are intended to include the plural forms as well, unless the context clearly indicates otherwise. It will be further understood that the terms "comprising", "including" and/or "having" and other conjugations of these terms, when used in this specification, specify the presence of stated features, integers, steps, operations, elements, and/or components, but do not preclude the presence or addition of one or more other features, integers, steps, operations, elements, components, and/or groups thereof.

The terminology used herein should not be understood as limiting, unless otherwise specified, and is for the purpose of describing particular embodiments only and is not intended to be limiting of the disclosed subject matter. While certain embodiments of the disclosed subject matter have been illustrated and described, it will be clear that the disclosure is not limited to the embodiments described herein. Numerous modifications, changes, variations, substitutions and equivalents are not precluded.

The invention claimed is:

1. A sublingual delivery device comprising:
    a device body having a proximal end and a distal end, said device body comprising:
        a delivery button configured to operate the sublingual delivery device;
        an ampoule carrying liquid comprising an ampoule seal;
        a threaded rod configured to push the ampoule seal towards the proximal end of the device body;
        a joints mechanism configured to convert vertical motion of the delivery button to horizontal motion of the threaded rod;
    an adjustment knob configured to set the volume of liquid to be delivered by the sublingual delivery device by adjusting a rotation degree of the knob, said adjustment knob located at the distal end of said device body; and
    a mouthpiece made of a biocompatible material configured to be placed into and have a shape that conforms to the shape of a mouth of a user, said mouthpiece located at the proximal end of said device body, and said mouthpiece surrounding a hollow needle configured to penetrate the ampoule and deliver liquid from the ampoule into the mouth of the user;
    wherein said joints mechanism comprises a ring arm, left and right vertical arms, and left and right arms, said ring arm connected to the left and right arms via a first corresponding joint, and said left and right arms are connected to the left and right vertical arms via a second corresponding joint,
    wherein actuation of the delivery button is restricted to a linear movement in a vertical direction, and when the delivery button is pressed vertically downwards, the left and right vertical arms are pushed down, thereby pulling the left and right arms down and towards the proximal end of the device body, which in turn pulls the ring arm towards the proximal end of the device body, to thereby pull the threaded rod towards the proximal end of the device body,
    further wherein the entire joints mechanism is encapsulated within the device body.

2. The sublingual delivery device of claim 1, wherein said right vertical arm is connected to the corresponding right arm, and the left vertical arm is connected to the corresponding left arm, wherein said right and left arms are in turn connected to the ring arm that is horizontally pushed towards the distal end of the device body once the right and left vertical arms are vertically pushed by the delivery button.

3. The sublingual delivery device of claim 1, wherein said device body further comprises a spring located between the adjustment knob and the threaded rod.

4. The sublingual delivery device of claim 1, wherein said device body further comprises a display.

5. The sublingual delivery device of claim 4, wherein said display displays the set volume of liquid to be administered by the sublingual delivery device.

6. The sublingual delivery device of claim 5, wherein said display further displays a timer counting down a recommended time for holding the liquid in a sublingual cavity of the user, said recommended time is determined based on the type of liquid.

7. The sublingual delivery device of claim 4, wherein said display displays the name of the liquid carried within the ampoule, the volume of liquid to be administered, the liquid volume carried by the ampoule, the volume remained in the ampoule, power source status of the sublingual delivery device, a timer, and/or any combination thereof.

8. The sublingual delivery device of claim 1, wherein said sublingual device is configured to provide an accurate volume of 0.05 mL with a variance of no more than 0.01 ml.

9. The sublingual delivery device of claim 1, wherein said sublingual delivery device further comprising a processor configured to collect data related to time and volume of delivered liquid.

10. The sublingual delivery device of claim 9, wherein said sublingual delivery device is configured to send the collected data to a computerized device in communication with said sublingual delivery device.

11. The sublingual delivery device of claim 1, wherein said sublingual delivery device is controlled by a computerized device.

12. The sublingual delivery device of claim 1, wherein said hollow needle is made of glass.

13. The sublingual delivery device of claim 1, wherein said hollow needle is made of a crystalline material.

14. The sublingual delivery device of claim 1, wherein said liquid comprises one or more pharmaceutical compositions.

15. The sublingual device of claim 1, wherein said mouthpiece is soft to protect the gum and sublingual surface of the mouth of the user.

16. A system for monitoring sublingual delivery, said system comprising:
    a sublingual delivery device according to claim 1;
    a computerized device in communication with said sublingual delivery device; and
    a cloud-based database in communication with the computerized device,
    wherein said sublingual delivery device is configured to collect data, send it to the computerized device, and said computerized device is configured to send the data to be stored in the cloud-based database.

17. The system of claim 16, wherein said data comprises volume intake of the liquid, time of intake, remaining volume in ampoule, temperature of ampoule, expiration date of ampoule, user symptoms, user's physical state and/or any combination thereof.

18. The system of claim 16, wherein the collected data stored in the cloud-based database is configured to be sent to a physician or health care provider to monitor patient condition.

19. A method for sublingual delivery, said method comprising:
- providing a sublingual delivery device according to claim 1;
- setting a volume of liquid to be delivered by rotating the adjustment knob;
- placing the sublingual delivery device inside a sublingual cavity of the user;
- pressing the delivery button, thereby ejecting liquid from the mouthpiece through the hollow needle into the sublingual cavity; and
- receiving time and volume of delivered liquid via a computerized device in communication with the sublingual delivery device.

20. The sublingual delivery device of claim 1, wherein said device further comprises a linear encoder configured to measure the location of the threaded rod, thereby to measure the amount of liquid that is delivered and the remaining volume of liquid carried within the ampoule.

21. The sublingual delivery device of claim 1, wherein said device further comprises a radial encoder configured to measure the rotation of the adjustment knob, thereby to measure the amount of liquid that is set to be delivered.

\* \* \* \* \*